US005688693A

United States Patent [19]

Fine et al.

[11] Patent Number: 5,688,693
[45] Date of Patent: Nov. 18, 1997

[54] METHOD AND SYSTEM FOR SAMPLING AND DETERMINING THE PRESENCE OF CONTAMINANTS IN RECYCLABLE PLASTIC MATERIALS

[75] Inventors: David H. Fine, Lincoln; Freeman W. Fraim, Lexington, both of Mass.; Stephen J. MacDonald, Salem, N.H.; Alex Malaspina, Atlanta, Ga.; Forrest Lee Bayer, Norcross, Ga.; Dirck vanBuren Myers, Atlanta, Ga.

[73] Assignee: The Coca-Cola Company, Atlanta, Ga.

[21] Appl. No.: 639,757

[22] Filed: Apr. 29, 1996

Related U.S. Application Data

[60] Division of Ser. No. 251,373, May 31, 1994, Pat. No. 5,569,606, which is a continuation-in-part of Ser. No. 890,863, Jun. 1, 1992, Pat. No. 5,352,611.

[51] Int. Cl.[6] .................................................. G01N 21/90
[52] U.S. Cl. ........................ 436/43; 436/50; 436/172; 422/62; 422/80; 422/83; 422/105; 422/119; 209/3; 209/523; 241/19; 241/24.1; 241/76; 241/79; 241/DIG. 38
[58] Field of Search ............................ 436/43, 47, 53, 436/106, 172, 165, 50, 55; 422/80, 83, 82.05, 82.08, 50, 62, 105, 119; 209/3, 523, 3.1; 241/19, 24.1, 76, 79, 99, DIG. 38; 73/23.35, 23.41

[56] References Cited

U.S. PATENT DOCUMENTS

| | | |
|---|---|---|
| 3,533,744 | 10/1970 | Unger . |
| 3,763,877 | 10/1973 | Lieb . |
| 3,845,309 | 10/1974 | Helm et al. . |
| 4,193,963 | 3/1980 | Bruening et al. . |
| 4,257,777 | 3/1981 | Dymond et al. . |
| 4,265,855 | 5/1981 | Mandle et al. . |
| 4,580,440 | 4/1986 | Reid et al. . |
| 4,761,268 | 8/1988 | Andersen et al. . |
| 4,775,633 | 10/1988 | Rounbehler . |
| 4,830,192 | 5/1989 | Plester et al. . |
| 4,843,016 | 6/1989 | Fine . |
| 4,858,768 | 8/1989 | Plester . |
| 4,871,118 | 10/1989 | Maloney . |
| 4,880,120 | 11/1989 | Myers et al. . |
| 4,899,573 | 2/1990 | Dimmick et al. . |
| 4,909,089 | 3/1990 | Achter et al. . |
| 4,909,090 | 3/1990 | McGown et al. . |
| 5,067,616 | 11/1991 | Plester et al. . |
| 5,096,130 | 3/1992 | Gulmini . |
| 5,108,705 | 4/1992 | Rounbehler et al. . |
| 5,115,987 | 5/1992 | Mithal . |
| 5,143,308 | 9/1992 | Hally et al. ........................ 241/76 |
| 5,152,963 | 10/1992 | Wreyford . |
| 5,225,137 | 7/1993 | Sadr . |

*Primary Examiner*—Long V. Le
*Attorney, Agent, or Firm*—Birch, Stewart, Kolasch & Birch, LLP

[57] ABSTRACT

An inspection system for sampling and determining the presence of residues of contaminants within plastic materials to be recycled from used plastic materials such as plastic beverage bottles or plastic food containers includes a chemical sniffing apparatus, or alternatively an optical scanner, for detecting the contaminants as the plastic materials are rapidly moved along a conveyor past a series of stations. Recycled food or beverage bottles are fed through a shredder in-line with the conveyor and the shredded plastic material from the bottles is fed to a washer. The bottles and shredded material may be tested for contaminants at any location in an in-line process. In one exemplary system first the bottles are tested prior to entry into the shredder in order to remove bottles containing gross contaminants. Second the shredded material emerging from the shredder is immediately tested for contaminants at an elevated temperature caused by the shredding process and contaminated materials are separated or sorted out from the uncontaminated material. Third, the materials are again tested for contaminants as they emerge from the washer once again taking advantage of the elevated temperature of the materials which is conducive to the emission of vapors of the contaminants. Contaminated materials are again sorted from the uncontaminated supply of materials to be used for the fabrication of new plastic food or beverage bottles.

12 Claims, 2 Drawing Sheets

METHOD AND SYSTEM FOR SAMPLING AND DETERMINING THE PRESENCE OF CONTAMINANTS IN RECYCLABLE PLASTIC MATERIALS

This application is a divisional of U.S. application Ser. No. 08/251,373, filed on May 31, 1994, now U.S. Pat. No. 5,569,606 which is a continuation-in-part of prior U.S. application Ser. No. 07/890,863 filed Jun. 1, 1992, now U.S. Pat. No. 5,352,611, and assigned to the same assignee as the present invention described herein, the entire contents of which are hereby incorporated by reference.

BACKGROUND OF THE INVENTION

The present invention relates to an inspection system for sampling and determining the presence of certain substances, such as residues of contaminants within plastic materials to be recycled from containers such as plastic polyethylene terephthalate (PET) beverage bottles or plastic food containers. More specifically, the present invention relates to an improved sampling and analyzing system and method for determining the presence of substances such as residues of contaminants in plastic materials from recycled articles such as beverage bottles or other containers—e.g., as the material is rapidly moved along a conveyor past a series of test stations in a material washing and sorting system.

In many industries, including the beverage industry, products are packaged in containers which are returned after use, washed and refilled. Typically refillable containers, such as beverage bottles, are made of glass which can be easily cleaned. These containers are washed and then inspected for the presence of foreign matter.

Glass containers have the disadvantage of being fragile and, in larger volumes, of being relatively heavy. Accordingly, it is highly desirable to use plastic containers because they are less fragile and lighter than glass containers of the same volume. However, plastic materials can absorb a variety of compounds which may later be desorbed into the product thereby potentially adversely affecting the quality of the product packed in the container. Examples of such compounds include but are not limited to ammonia, organic nitrogenous compounds, and hydrocarbons including gasoline and various cleaning fluids including soaps and detergents.

However, if these plastic containers, or the materials from which each is made can be reliably inspected for contaminants of very high sensitivity, contaminated plastic bottles or materials can be separated from uncontaminated containers or materials, and the good containers or materials can be recycled.

The aforementioned U.S. application Ser. No. 07/890,863 describes inspection techniques for determining the presence of contaminants in used, plastic beverage containers, or in shredded or flaked plastic material from which the containers were made.

The present invention is directed to improvements to the techniques described in the prior application Ser. No. 07/890,863, now U.S. Pat. No. 5,352,611 regarding recycling of plastic materials, including materials from which such used plastic beverage containers were made.

In order to recycle plastic materials such as from PET beverage bottles for use in the fabrication of new bottles, it is necessary to ensure that the recycled material does not contain any potentially harmful contaminants of the types described hereinbefore.

While various efforts have been made for removing unwanted contaminated plastics from an incoming stream of beverage bottles, and then shredding the bottles and thoroughly washing the shredded plastic material so as to remove potentially harmful contaminants from the shredded or flaked material, a need in the art exists for improved inspection of recycled plastic materials. In particular, it would be advantageous to have on-line, real-time, chemical monitoring of recycled plastic materials such as bottles or resulting flake at any stage of processing, particularly at any stage of pre-processing, including sortation, cleaning, washing, flaking, pelletizing and preform and/or bottle manufacturing to ensure that badly contaminated material has been removed from the recycled material.

SUMMARY OF THE INVENTION

Accordingly, it is a primary object of the present invention to provide a method and system for detecting the presence or absence of specific substances—e.g., contaminants including but not limited to ammonia, organic nitrogenous compounds and hydrocarbons, in plastic materials.

It is another object of the present invention to provide a system and method for detecting specific contaminants in articles made of plastic materials, or in shredded, pelletized, or flaked plastic materials, as the articles or materials move rapidly along a conveyor.

It is another object of the present invention to provide a system and method for sampling and analyzing residues in materials as they move along a conveyor.

It is still another object of the present invention to provide a system and method for sampling and analyzing residues in materials moving along a conveyor without contacting the materials being tested with any of the sampling and analyzing mechanisms.

It is yet another object of the present invention to provide a method for inspecting used plastic beverage containers for contaminants, shredding the containers into constituent pieces thereof and washing the constituent pieces in a continuous, in-line process.

The objects of the present invention are fulfilled by providing a method of sampling and determining the presence of certain volatiles in plastic materials to be recycled comprising the steps of: providing a supply of plastic materials to be recycled; directing fluid (usually a jet of air or $CO_2$ gas) at said materials in order to displace at least a portion of volatiles therein to positions spaced from the materials to form a sample cloud at a region spaced from the materials; evacuating a sample of said portion of the volatiles so displaced by applying suction to the sample cloud at said regions spaced from said materials; and analyzing the sample evacuated to determine the presence or absence of volatiles of said contaminants in said materials. The procedure may also involve optical scanning of the plastic for non volatile contaminants. This is carried out in real time as the bottle or shreds pass by the sampling point. Other fluids which may be directed at the materials may include but are not limited to liquids such as aqueous sodium carbonate ($NaCO_3$) which enhances liberation of ammonia or amines from the materials. However, $NaCO_3$ would not be used at an inspection station located after a washer—i.e., to inspect plastic materials immediately following their washing or at any other location further downstream.

In a preferred embodiment the supply of materials is provided from used beverage containers of plastic by an in-line shredder or flaker in-line with the inspection and washing conveyor which shreds or flakes the plastic containers into constituent pieces thereof which are inspected for contaminants, sorted and washed.

It is a discovery of the present invention, that the shredding of the plastic containers into pieces, heats the pieces to a temperature sufficient to vaporize some of the contaminants therein in order to emit volatiles thereof. Accordingly, it is particularly advantageous to analyze the emitted volatiles either during or immediately after the shredding of the containers.

It is a further discovery of the present invention that it is particularly advantageous to test the shredded plastic materials just after the washing process, again due to the fact that there are high temperatures associated with the washing process that will liberate volatiles of contaminants in the plastic material if any are present.

It is still a further discovery of the present invention that it is important to maintain the temperature of the washed shredded material below a level that would emit detectable levels of vapors derived from the plastic material itself which would create background interference with volatiles of any contaminants emitted from the plastic materials.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitative of the present invention and wherein.

DETAILED DESCRIPTION OF PREFERRED EMBODIMENTS

Figure 1:
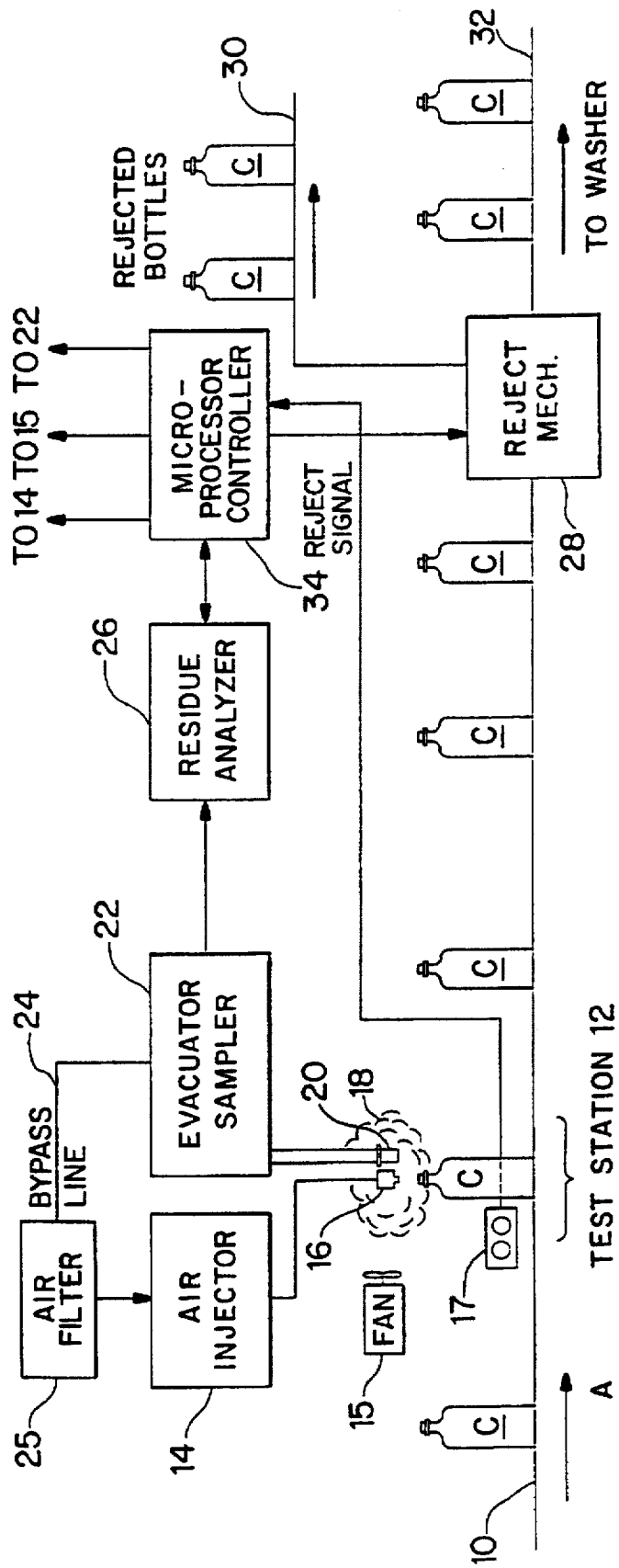
FIG. 1 is a schematic block diagram of the sampling and residue analyzing system of the invention described in U.S. application Ser. No. 07/890,863 illustrating a plurality of containers moving seriatim along a conveyor system through a test station, reject mechanism and washer station.

The system of FIG. 1 is fully disclosed in allowed parent application Ser. No. 07/890,863 filed Jun. 1, 1992, now U.S. Pat. No. 5,352,611 the entire disclosure of which is incorporated herein by reference.

Referring to FIG. 1 there is illustrated a conveyor 10 moving in the direction of arrow A having a plurality of uncapped, open-topped spaced containers C (e.g. plastic beverage bottles of about 1500 c.c. volume) disposed thereon for movement seriatim through a test station 12, reject mechanism 28 and conveyor 32 to a washer system. To achieve higher test rates containers C could be touching each other rather than spaced. The contents of containers C would typically include air, volatiles of residues of contaminants, if any, and volatiles of any products such as beverages which had been in the containers. An air injector 14 which is a source of compressed air is provided with a nozzle 16 spaced from but aligned with a container C at test station 12. That is nozzle 16 is disposed outside of the containers and makes no contact therewith. Nozzle 16 directs compressed air into containers C to displace at least a portion of the contents of the container to thereby emit a sample cloud 18 to a region outside of the container being tested.

As an alternative to compressed air, $CO_2$ gas could be utilized as the injected fluid. Also the compressed air or $CO_2$ gas could be heated to enhance volatility of the compounds being tested.

The column of injected air through nozzle 16 into a container C would be typically of the order of about 10 c.c. to 50 c.c. for bottle speeds of about 200 to 1000 bottles per minute. A rate of 400 to 600 bottles per minute is possible and is compatible with current beverage bottle filling speeds. The desired test rate may vary with the size of the bottles being inspected and filled. Of course the bottles could be stationary or moving slower than 200 bottles per minute and the system would still work. Only about 10 c.c. of the container contents would be displaced to regions outside of the bottle to form sample cloud 18.

Also provided is an evacuator sampler 22 which may comprise a vacuum pump or the like coupled to a sampling tube or conduit 20. The tube is mounted near, and preferably downstream (e.g., about 1/16 inch) of the air injector 14 so as to be in fluid communication with sample cloud 18 adjacent to the opening at the top of containers C.

Neither nozzle 16 nor tube 20 contacts the containers C at test station 12; rather both are spaced at positions outside of the containers in close proximity to the openings thereof. This is advantageous in that no physical coupling is required to the containers C, or insertion of probes into the containers, which would impede their rapid movement along conveyor 10 and thus slow down the sampling rate. High speed sampling rates of from about 200 to 1000 bottles per minute are possible with the system and method of the present invention. The conveyor 10 is preferably driven continuously to achieve these rates without stopping or slowing the bottles down at the test station.

A bypass line 24 is provided in communication with the evacuator sampler 22 so that a predetermined portion (preferably about 90%) of the sample from cloud 18 entering tube 20 can be diverted through bypass line 24. The remaining sample portion passes to a residue analyzer 26, which determines whether undesirable substances are present, and then is exhausted. One purpose of diverting a large portion of the sample from cloud 18 is to reduce the amount of sample passing from evacuator sampler 22 to residue analyzer 26 in order to achieve high speed analysis. This is done in order to provide manageable levels of samples to be tested by the residue analyzer 26. Another purpose for diverting a portion of the sample is to be able to substantially remove all of sample cloud 18 by evacuator 22 from the test station area and divert the excess through bypass line 24. In a preferred embodiment the excess portion of the sample passing through bypass line 24 is returned to air injector 14 for introduction into the subsequent containers moving along conveyor 10 through nozzle 16. However, it would also be possible to simply vent bypass line 24 to the atmosphere.

It should be understood that sample cloud 18 could be analyzed in situ without transporting it to a remote analyzer such as 26. It could also be transported to analyzer 26 by blowing rather than sucking.

A microprocessor controller 34 is provided for controlling the operation of air injector 14, evacuator sampler 22, residue analyzer 26, a reject mechanism 28 and an optional fan 15. Container sensor 17 including juxtaposed radiation source and photodetector is disposed opposite a reflector (not shown) across conveyor 10. Sensor 17 tells controller 34 when a container arrives at the test station and briefly interrupts the beam of radiation reflected to the photodetector. Optional fan 15 is provided to generate an air blast towards sample cloud 18 and preferably in the direction of movement of containers C to assist in the removal of sample cloud 18 from the vicinity of test station 12 after each container C is sampled. This clears out the air from the region of the test station so that no lingering residues from an existing sample cloud 18 can contaminate the test station area when successive containers C reach the test station for sampling. Thus, sample carryover between containers is precluded. The duty cycle for operation of fan 15 is controlled by microprocessor 34 as indicated diagrammatically in FIG. 1. Preferably fan 15 is continuously operating for the entire time the rest of the system is operating.

A reject mechanism 28 receives a reject signal from microprocessor controller 34 when residue analyzer 26 determines that a particular container C is contaminated with a residue of various undesirable types. Reject mechanism 28 diverts contaminated rejected bottles to a conveyor 30 and allows passage of uncontaminated, acceptable bottles to a washer (not shown) on a conveyor 32.

An alternative option is to place the bottle test station downstream of the bottle washer in the direction of conveyor travel, or to place an additional test station and sample and residue analyzing system after the washer. In fact it may be preferable to position the test station and system after the washer when inspecting bottles for some contaminants. For example, if the contaminant is a hydrocarbon, such as gasoline which is insoluble in water, it is easier to detect residues of hydrocarbons after the bottles have been washed. This is because during the washing process in which the bottles are heated and washed with water, water soluble chemical volatiles are desorbed from the bottles by the heating thereof and then dissolved in the washing water. Certain hydrocarbons, on the other hand, not being water soluble, may then be sampled by a sampler 22 downstream of the washer, to the exclusion of the dissolved, water-soluble chemicals. Therefore, the detection of such hydrocarbons can be performed without potential interference from other water soluble chemicals if the bottles pass through a washer before testing.

The materials to be inspected are not limited to substances in containers. For example, the method and system of FIG. 1 could be used to detect volatiles adsorbed in shredded strips or flakes of the bottles, or plastic stock to be recycled for manufacturing new plastic beverage bottles or food containers or other articles of plastic. This shredded or flaked plastic stock could be placed directly on a conveyor belt 10 and passed through test station 12 of FIG. 1; or the plastic stock could be placed in baskets, buckets or other types of containers disposed thereon and inspected in batches.

Figure 2:
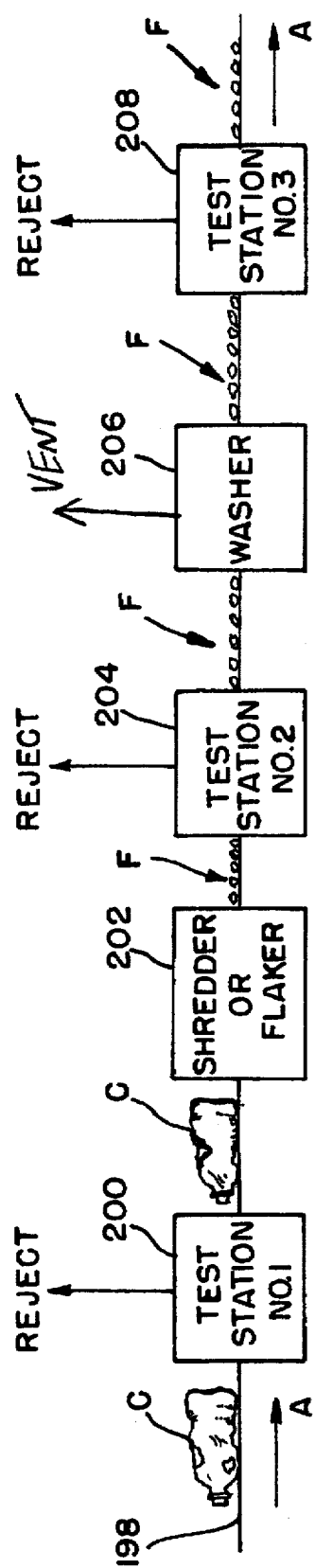
FIG. 2 is a schematic block diagram of a system and method for inspecting, shredding, washing and sorting recyclable plastic materials according to the present invention.

The system for analyzing volatiles emitted from containers C at test station 12 in FIG. 1 will be referred to hereinafter with respect to embodiments of the present invention illustrated in FIG. 2 as chemical "sniffing". FIG. 2 illustrates an in-line conveyor system including a conveyor 198 on which a plurality of plastic containers C move through a first test station 200, and into a shredder or flaker 202. Shreds or flakes F emerging from shredder or flaker 202 pass through a test station 204, where contaminated flakes are rejected and separated from cleaner flakes F on their way to a washer 206. The shredded or flaked material F emerging from washer 206 is again inspected at a test station 208, and still contaminated flakes of material are rejected. Substantially clean and pure flakes F to be utilized in the fabrication of new plastic containers emerge on conveyor 10 from test station 3.

Each of the test stations 200, 204 and 208 in the system of FIG. 2 preferably contains a chemical "sniffer" such as the system disclosed in FIG. 1 at test station 12.

It should be understood that additional test stations could follow test station 208. For example, there could be a flake pelletized after station 208 and a test station following the pelletizer; an additional test station following a preform manufacturing station for new bottles to test the preforms; and another test station after a blow molder which blows the preform into new bottles.

There are three different stages of the process illustrated in FIG. 2 where chemical sniffing of the plastic flakes F of material can be most effective. The first two sampling points at test stations 200 and 204 are designed to remove the contaminated material before it goes into the washing process in washer 206. If the chemical sniffing processes at test stations 200 and 204 are effective, then the effectiveness of the washing step at washer 206 is less critical. This may allow use of an inexpensive or cost-effective washer 206.

Testing and sampling of the incoming containers C at test station 200 of FIG. 2 is conducted to find gross contaminants in the containers and to minimize cross-contamination in other steps of pre-processing. The containers C are typically in the form of crushed and/or punctured bottles at this point, and may be in prone rather than upright position. Monitoring will, for example, find the bottles where liquid has spilled out and has cross contaminated other bottles on their way to the shredder 202. This step is important since a bottle full of engine oil, for example, may contaminate several other bottles if the oil spills.

Containers C which have passed through test station 200, and have not been rejected, pass into shredder 202. Heat is generated in the shredder 202 as the containers are broken down into pieces. Temperatures of up to 200° F. are generated, which can serve to drive off the contaminants so that they can be more readily detected. An additional advantage of sampling the shredded material as it emerges from shredder 202 at test station 204, is that contaminants released from the shredding of a single contaminated bottle will not have contaminated too much other material. Thus, sampling the fumes from the shredder at test station 204 could lead to the rejection from the process stream of flakes of material F from the bottle in question together with materials from just a few adjacent bottles.

Sampling at the shredder 202, or as close to the newly shredded material emerging from shredder 202 as possible, is needed so as to avoid contaminating a large amount of flakes F. That is, any contaminated flakes emerging from shredder 202 are immediately detected at test station 204, and rejected in order to avoid contaminating a substantial quantity of flakes on the conveyor 198.

A third test station 208, is designed to detect flakes F as they emerge from washer 206 in order to monitor the washing process. Again, monitoring is best accomplished where the temperatures are high enough to assist in the emission of volatiles of contaminants from the flakes of material. Temperatures in the washer are typically from about 190° F. to about 210° F. Monitoring of the post-washed flakes F is for quality assurance purposes, since the detection of contaminants at this point in the process will require the automatic rejection of a considerable amount of material due to the mixing of good and bad flakes F in the washing process.

It is a discovery of the present invention that the temperature of the wash solution used in the washer 206 or in a pelletizer or preform maker must be kept below a temperature at which the plastic material being inspected will vaporize. Such vaporization would produce detectable background volatiles which would tend to interfere with detection of volatiles relating to contaminants within the materials. For example, tests were performed on flakes from PET beverage bottles in order to determine the ability of the analyzing apparatus of the present invention to sniff the material without interference from background volatiles of the PET material itself. Six temperatures were studied, as shown below:

| Temperature °F. | Observation |
| --- | --- |
| 80 | No background response from PET vapors |
| 200 | No background response from PET vapors |
| 300 | No background response from PET vapors |
| 400 | No background response from PET vapors |
| 650 | No background response from PET vapors |
| 750 | Background response observed |

From the above results it was concluded that PET flakes can be chemically sniffed at temperatures of up to about 650° F. without any effects from the PET itself on the accurate detection of contaminants within the PET flakes.

However, typically the highest temperatures encountered where sniff tests would be made would occur at the pelletizing and preform stations, and those temperatures would likely not exceed about 570° F.

Another observation from these experiments is that the washing procedure must preferably vent the hot vapors from the process stream or risk contamination of all of the PET material that is in contact with contaminated vapors in the washer. This is important and differs from conventional washers since the tendency in prior art systems is to use enclosed systems washers so as to conserve heat and minimize energy cost. However, washer 206 has a vent, such as vent 210, to carry hot vapors away from the PET flakes. Shredder 202 may also include a vent for hot vapors associated with the shredding process.

It should be understood that the present invention may be modified as would occur to one of ordinary skill in the art without departure from the spirit and scope of the present invention, and all such modifications as would be obvious to one skilled in the art are intended to be included within the scope of the following claims.

What is claimed is:

1. A method of determining whether plastic material moving along a conveyor obtained from used containers is free of volatiles of contaminants and sorting that material so that the material can be recycled to produce new containers, comprising the steps of:

providing a supply of used containers to the conveyor;

testing each used container for volatiles of contaminants therein;

separating and removing contaminated containers from the conveyor;

breaking each remaining container into pieces of said material, said breaking causing said pieces to be heated to temperatures sufficient to vaporize the contaminants and emit volatiles thereof;

testing said volatiles to determine the presence or absence of said contaminants in said materials;

separating and removing pieces of material containing contaminants from the conveyor;

washing the pieces of materials remaining on the conveyor in a heated fluid to remove a portion of contaminants and to emit detectable levels of volatiles of the contaminants therein;

testing the volatiles of the contaminants from pieces which have been washed to determine the presence or absence of contaminants in the materials; and separating pieces containing contaminants from those not containing contaminants.

2. The method of claim 1, wherein each step of testing comprises the steps of:

directing fluid at said container or pieces of materials in order to displace at least a portion of volatiles therein to positions spaced from the materials to form a sample cloud at a region spaced from the materials;

evacuating a sample of said portion of the volatiles so displaced by applying suction to the sample cloud at said region spaced from said materials; and analyzing the sample evacuated to determine the presence or absence of said contaminants in the materials.

3. The method of claim 2 including the additional step of:

maintaining the temperature of washed material below a level that would emit detectable levels of vapors derived from the plastic material itself.

4. The method of claim 3 wherein the plastic material is PET and the temperature is maintained below about 650° F.

5. The method of claim 1 including the additional step of:

maintaining the temperature of washed material below a level that would emit detectable levels of vapors derived from the plastic material itself.

6. The method of claim 5 wherein the plastic material is PET and the temperature is maintained below about 650° F.

7. A system for determining whether plastic material moving along a conveyor obtained from used containers is free of volatiles of contaminants and sorting that material so that the material can be recycled to produce new containers, comprising:

a supply of used containers on the conveyor;

first means for testing each used container for volatiles of contaminants therein;

first means for separating and removing contaminated containers from the conveyor;

means for breaking each remaining container into pieces of said material, said breaking causing said pieces to be heated to temperatures sufficient to vaporize the contaminants and emit volatiles thereof;

second means for testing said volatiles to determine the presence or absence of said contaminants in said materials;

second means for separating and removing pieces of material containing contaminants from the conveyor;

means for washing the pieces of materials remaining on the conveyor in a heated fluid to remove a portion of contaminants and to emit detectable levels of volatiles of the contaminants therein;

third means for testing the volatiles of the contaminants of pieces which have been washed to determine the presence or absence of contaminants in the materials; and third means for separating pieces containing contaminants from those not containing contaminants.

8. The system of claim 7 wherein each means for testing comprises:

means for directing fluid at said container or pieces of materials in order to displace at least a portion of volatiles therein to positions spaced from the materials to form a sample cloud at a region spaced from the materials;

means for evacuating a sample of said portion of the volatiles so displaced by applying suction to the sample cloud at said region spaced from said materials; and means for analyzing the sample evacuated to determine the presence or absence of said contaminants in the materials.

9. The system of claim 8 further including:

means for maintaining the temperature of washed material below a level that would emit detectable levels of vapors derived from the plastic material itself.

10. The system of claim 9 wherein the plastic material is PET and the temperature is maintained below about 650° F.

11. The system of claim 7 further including:

means for maintaining the temperature of washed material below a level that would emit detectable levels of vapors derived from the plastic material itself.

12. The system of claim 11 wherein the plastic material is PET and the temperature is maintained below about 650° F.

* * * * *